(12) United States Patent
Halliday

(10) Patent No.: US 6,840,098 B2
(45) Date of Patent: Jan. 11, 2005

(54) ROADWAY FRICTION TESTER AND METHOD

(76) Inventor: Donald R. Halliday, 5312 Cascade Dr., Powell, OH (US) 43065

( * ) Notice: Subject to any disclaimer, the term of this patent is extended or adjusted under 35 U.S.C. 154(b) by 0 days.

(21) Appl. No.: 10/352,351

(22) Filed: Jan. 27, 2003

(65) Prior Publication Data

US 2004/0144167 A1 Jul. 29, 2004

(51) Int. Cl.$^7$ .............................................. G01M 17/02
(52) U.S. Cl. ................................................. 73/146; 73/9
(58) Field of Search ....................................... 73/147, 9

(56) References Cited

U.S. PATENT DOCUMENTS

| | | | | |
|---|---|---|---|---|
| 4,098,111 A | * | 7/1978 | Hardmark et al. ................ | 73/9 |
| 4,594,878 A | * | 6/1986 | Abe et al. ......................... | 73/9 |
| 4,662,211 A | * | 5/1987 | Strong .............................. | 73/9 |
| 4,909,073 A | * | 3/1990 | Takahashi et al. ............ | 73/146 |
| 4,958,512 A | * | 9/1990 | Johnsen ............................ | 73/9 |
| 5,561,244 A | * | 10/1996 | Olesky et al. ................ | 73/146 |
| 5,851,086 A | * | 12/1998 | Kurasako ...................... | 404/94 |
| 5,900,531 A | * | 5/1999 | Mani et al. ....................... | 73/9 |
| 6,192,736 B1 | * | 2/2001 | Clem ................................ | 73/9 |
| 6,321,586 B1 | * | 11/2001 | Wojtowicz et al. .............. | 73/9 |
| 6,427,519 B2 | * | 8/2002 | Ueda et al. ...................... | 73/9 |
| 6,463,784 B2 | * | 10/2002 | Kashiwagi et al. .............. | 73/9 |
| 6,546,790 B1 | * | 4/2003 | Halliday ..................... | 73/146 |

* cited by examiner

Primary Examiner—Edward Lefkowitz
Assistant Examiner—Andre Allen
(74) Attorney, Agent, or Firm—Mueller and Smith, LPA

(57) ABSTRACT

A method for measuring road surface friction of a road surface uses a vehicle that moves across the road surface. An auxiliary independent wheel is interposed between the vehicle and the road surface. The auxiliary wheel is freely rotatable by movement of the vehicle and is toed in (skewed) with respect to a direction of travel of the vehicle so as to create an axial force on the auxiliary wheel. The axial force on the auxiliary wheel is isolated and measured while the vehicle moves across the road surface. The measured axial force is correlated with the road surface friction.

33 Claims, 6 Drawing Sheets

ROADWAY FRICTION TESTER AND METHOD

CROSS-REFERENCE TO RELATED APPLICATIONS

None

STATEMENT REGARDING FEDERALLY SPONSORED RESEARCH

Not applicable.

BACKGROUND OF THE INVENTION

The present invention generally relates to a practical system of measuring road surface friction using an auxiliary wheel and more particularly to a system wherein a switch in the cab deploys the measuring wheel and the in-cab display gives a continuous reading of road surface friction as soon as the wheel rotates. The road friction tester ("RFT") is designed for use in the trucking industry to determine road surface grip where driving conditions may be hazardous.

Most currently used, practical, devices, which measure road friction, require either a dedicated vehicle for operation or are towed behind a vehicle. It is desirable to measure the road traction, for example, in the winter as ice is forming and while snow and ice is being removed from the road. The knowledge of road condition while the road is being treated is helpful in determining appropriate treatment of the road surface. Cost savings can be realized, but road safety would also be increased which would help all motorists. DE 34 09 040.1 recognizes the need to measure the lateral force exerted against a wheel rotating in a straight line. No practical implementation for this recognition is given, however.

Most road friction measurement devices require a wheel to be skidded against the road in the same direction as the vehicle. The force, which resists forward motion, is measured. This particular layout requires a tire, which runs at a slower of faster speed than road speed. This requirement results in high tire wear, water must flood the contact patch and very large forces are developed. There have been other means of measuring the friction using a tire or wheel skew to the motion vector of the vehicle, but many have been abandoned due to complexity or reliability issues.

U.S. Pat. No. 5,821,434 is a method for determining the grip performance of a vehicle. To measure the grip performance of a vehicle, a practical method of measuring the lateral force developed by a tire was required. The details of this method are described in U.S. Pat. No. 5,821,434. In synopsis, the rotating member and its bearing support are isolated from the wheel hangar by a linear bearing. The linear bearing allows the freedom of motion necessary for measurement of the force developed between the wheel support bearing and the hangar and an appropriately designed load cell measures this force. This patent is a development of this previous patent in that a similar method of determining the force is used, but the focus of the patent is to determine the frictional capacity of the road as opposed to the grip performance of a vehicle. The GEM device is the commercial embodiment for measuring grip performance of a vehicle.

The present invention is unique in that it extends the GEM device concept for taking road condition measurements for determining the condition of the road under adverse weather conditions in real time.

BRIEF SUMMARY OF THE INVENTION

The GEM device patents illustrate an elegant method of obtaining the lateral force developed by a tire mounted on a vehicle. The further simplification and adaptation of the GEM concept to the problem of measuring road friction would solve numerous implementation problems. The invention, then, is to add another wheel to the vehicle (or use an existing wheel), which is maintained at a skew angle relative to the direction of travel of the vehicle. This auxiliary wheel has, included, a GEM device, as outlined in the earlier patent, as well as a speed sensor. The GEM device has proven robust in the auto racing environment and the passenger car environment. A rugged version would be suitable to the task of measuring the friction of the road and be placed underneath the vehicle. The lateral load then is resolved to different grip levels corresponding to ice, snow, water on pavement, and dry pavement. This relationship then is conveyed to the driver of the truck who then, for example, can regulate the amount or type of roadway treatment based on this pertinent information. The inventive RFT device is designed to perform its duties causing no interference to the normal operation of any truck or road maintenance vehicle.

The inventive method for measuring road surface friction of a road surface uses a vehicle that moves across the road surface. An auxiliary independent wheel is interposed between the vehicle and the road surface. The auxiliary wheel is freely rotatable by movement of the vehicle and is toed in or toed out (skewed) with respect to a direction of travel of the vehicle so as to create an axial force on the auxiliary wheel. The axial force on the auxiliary wheel is isolated and measured while the vehicle moves across the road surface. The measured axial force is correlated with the road surface friction.

The invention uses in combination, a vehicle and a device affixed to the vehicle. The device for measuring road surface friction includes an auxiliary wheel mounted to the vehicle and between the vehicle and the road surface. The auxiliary wheel is toed in or toed out, loaded, and mounted on an axle for its free rolling. A calibrated force sensor is associated with the auxiliary wheel to measure the isolated axial force thereon. A converter displays the road friction and displays it to the vehicle operator or remotely.

Advantages of the present invention include a simple, yet reliable and rugged device for measuring road friction. Another advantage is that the road friction can be displayed directly to the vehicle operator in real time. A further advantage is that the device does not interfere with operation of the vehicle and can be retracted while not in use. A yet further advantage is that the device does not pick up debris on the roadway. Another advantage is that the mounted tire of the device does not skid across the roadway. A yet further advantage is that the device can utilize normal angles, loads, and tires. Yet another advantage is that the device provides real time readout and is susceptible to telemetry for remote readout. These and other advantage will be readily apparent to those skilled in the art based on the disclosure herein.

BRIEF DESCRIPTION OF THE DRAWINGS

For a fuller understanding of the nature and advantages of the present invention, reference should be made to the following detailed description taken in connection with the accompanying drawings, in which.

Figure 1:
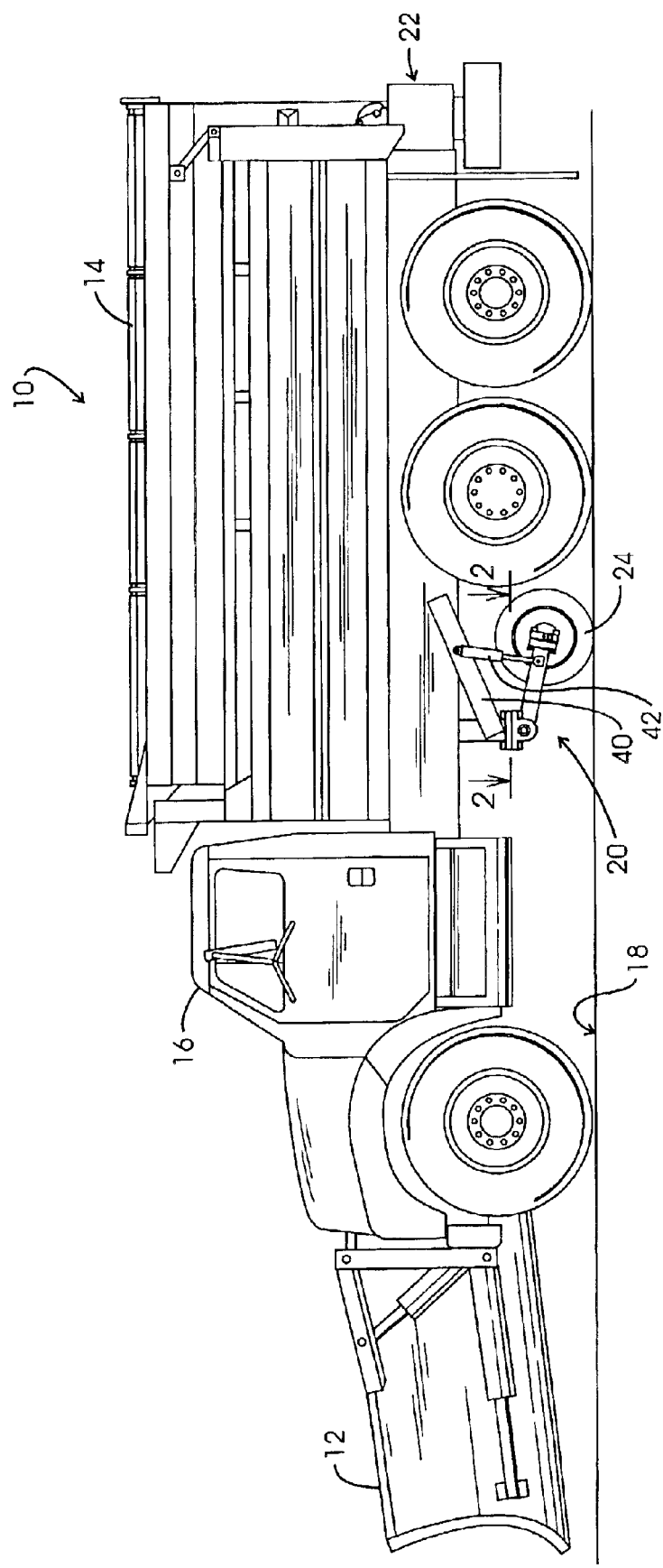
FIG. 1 is a side elevational view of a dump truck fitted with a front snowplow, a rear deployed salt or brine spreading system, and the inventive RFT embodied as a separate wheel riding underneath the truck bed and forward of the truck bed wheels.

The drawings will be discussed in detail in connection with the detailed description of the invention set forth below.

DETAILED DESCRIPTION OF THE INVENTION

The inventive RFT exhibits operational parameters making it quite useful to a truck operator, especially the operator of a snow plow/salt truck during wintertime. The design parameters met by the inventive RFT include:

To provide road friction value to the plow operator to aid in the safe operation of the vehicle.

To provide this road friction information in a practical and reliable manner and for the RFT to not adversely affect the plow drivability or handling.

To be capable of being installed behind an under mount plow.

To be a ruggedly built piece of truck equipment and not another example of laboratory equipment, which are not sufficiently robust to survive in this environment.

To be capable of easy use by the plow operator and to enhance, not impede, the road surface treatment process.

To aid in the effective use of surface treatment products.

The inventive RFT is able to sense dangerous road conditions well before they became noticeable to the plow operator and therefore can significantly aid in the safe operation of the plow vehicle. Without the RFT, the only sense the plow operator has of dangerous conditions is visual. High speed plowing now can be achieved in a safe manner.

The inventive RFT is effective at any time the auxiliary wheel is deployed, at any speed and under any conditions. The prototype RFT reported in the Example operated trouble free in testing on open roads and at an automotive winter test facility. There was no adverse affect on vehicle handling when using the RFT wheel. The RFT is easily operated from the cab. The unit provided reliable information with respect to the road surface conditions that can be used to aid in the effective use of surface treatment products. The sensitivity of the RFT will allow immediate evaluation of any surface treatment at any time. For protection of the unit the electronics can be located inside the sealed stainless steel measurement hub and in the cab of the truck. Also the cable between the two pieces is enclosed in a stainless steel braided Teflon line.

In order for the inventive RFT to be user friendly and intuitive to a snow plow operator, an LED (light emitting diode) bar graph was developed to display 10 equal divisions of green, 10 equal divisions of yellow, and 10 equal divisions of red lights. The lower the value of road friction the greater the number of lit LED lights. When red is lit the conditions are very low in road friction, indicating ice. Finally, the inventive RFT can be provided with a data link from the RFT to the existing data collection unit in the plow truck. The link to the data acquisition system is via an RS232 port.

The inventive RFT measures the threshold schedule for the ice, packed snow, water on concrete, and water on asphalt. These determinations are integrated into the inventive RFT described herein. The inventive RFT also is different from other devices on the market because it can be mounted to a vehicle, not towed behind it or incorporated into a dedicated vehicle. It is simple. Once the threshold scheduled is defined, the system will ride along and give a value of lateral grip.

The inventive RFT was to develop a combined speed and grip schedule to then develop an algorithm for determining the appropriate display of the level of safe driving speed. With the RFT measuring grip and speed, one can develop an algorithm for determining and displaying the appropriate speed for 'safe' motoring of the particular vehicle. This 'safe' speed could also be controlled with engine controls automatically if required. Another improvement of this device on other marketed products is that the RFT does not require complex ancillary systems to be operated. In the prototype implementation, hydraulic force is used to maintain contact of the auxiliary wheel with the ground. This force could be maintained with a static weight or a spring along with a damper. Other grip measurement systems require water to flood the tire road interface before the tire is placed in contact.

In summary, a system and method are disclosed for measuring the grip performance of a road surface by interposing an auxiliary independent wheel between a vehicle and the road surface. This wheel is free to rotate by its reaction on the road surface. No other system or method is required to either brake the wheel, or rotate the wheel at a speed greater than vehicle speed. This auxiliary wheel is mounted in a near vertical position and is skewed to the direction of travel in such a way as for the road surface to create a side force on this wheel relative to the vehicle. This side force, in an axial direction, then is measured between the wheel and the vehicle on which it is supported. The force representing the grip value of the road surface is measured between the wheel support system and the wheel by allowing the wheel to be able to be mechanically free to move in an axial direction. Most easily described the complete wheel assembly is mounted on single non-rotating shaft, which is securely fastened to the "A" arm holding the wheel on the vehicle. Around this shaft sits a linear bearing allowing axial motion of this wheel assembly relative to the shaft. The linear bearing sits in a non-rotating housing around which the bearing supporting the wheel is located. In locating the bearing on this non-rotating housing, the wheel is locked in an axial direction to the housing. The wheel is supported in a housing, which sits on the outside of the wheel bearing. The axial load then is measured by a load cell placed between the non-rotating housing and the A arm.

The ability to determine the frictional capacity of a road surface has tremendous safety implications. This ability to have the knowledge of the grip value of the road surface dynamically could be crucial to both trucking and snow ploughs applying de-icing agents to that surface.

Referring initially to FIG. 1, shown is a snow plow truck, 10, fitted with a forward-mounted plow, 12, and rearward-mounted salt bed, 14, for dispensing salt, brine, or other snow/ice melting compound and/or traction generating compound (e.g., cinders), a cab, 16, inside of which the operator sits. In all other respects, truck 10 can be common or uncommon in construction. Of advantage, is that the inventive RFT operates with trucks or other vehicles of common construction. The tires of truck 10 sit upon a roadway, 18, whose condition, vis-à-vis friction, is desired to be determined. An inventive RFT, 20, can been seen mounted underneath truck 10 rearward of plow 12 and forward of the salt/brine dispensing system, 22.

Figure 2:
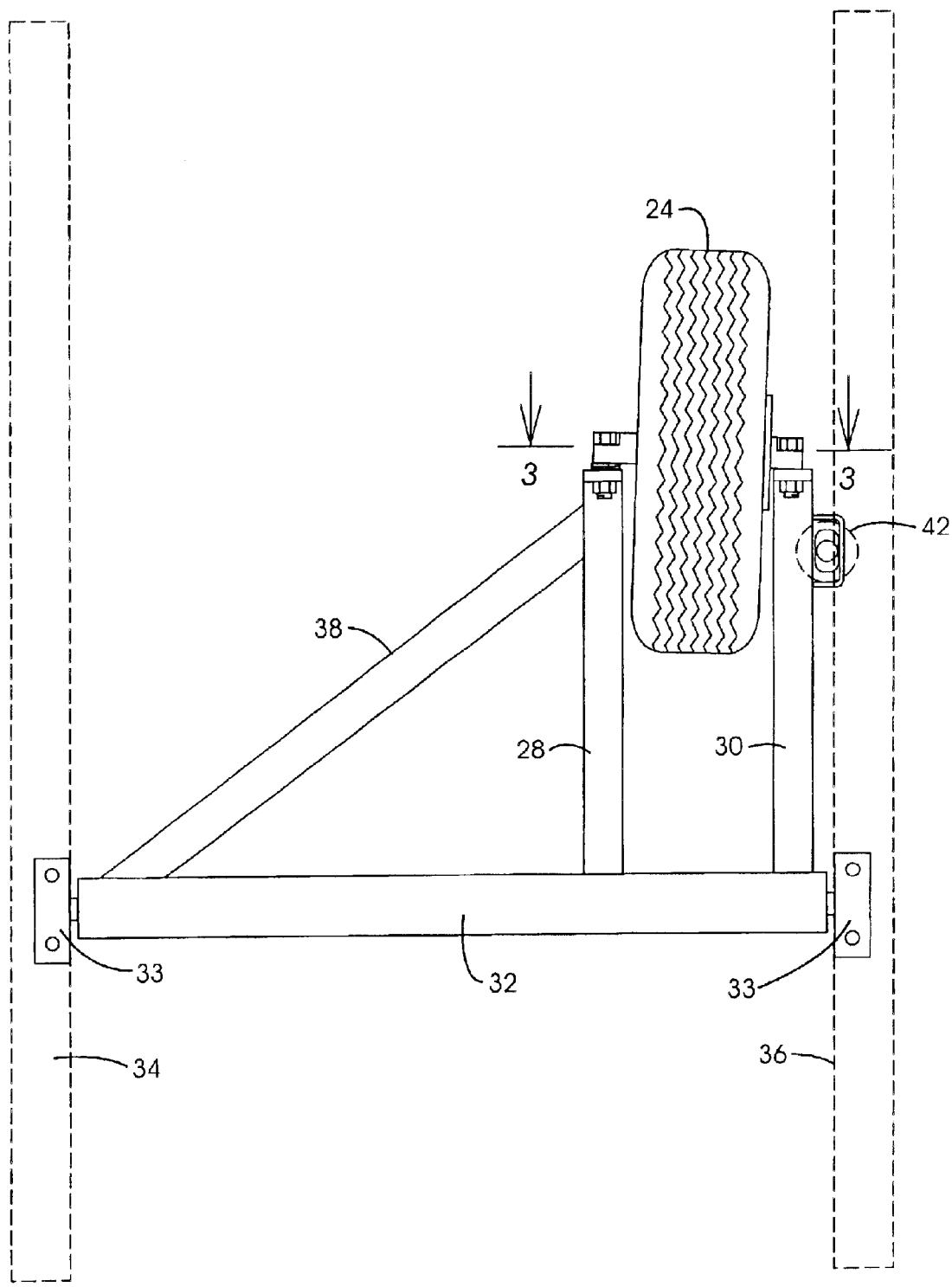
FIG. 2 is a cross-sectional view taken along line 2—2 of FIG. 1.

Referring to both FIGS. 1 and 2, RFT 20 is seen to include an auxiliary wheel/tire assembly, 24. The term wheel often will be used to denote both the tire as well as the wheel and tire assembly. An axle, 26, carries wheel assembly 24. The ends of axle 26 are carried by a pair of bars, 28 and 30, which in turn are connected to a transverse carrier bar, 32, which in turn is attached to the under frame of the truck bed, 34 and 36. A transverse bar, 38, braces bars 28 and 32 to add stability to assembly 20. Bars 38, 28, 30, and 32 denote a swing arm, which is able to rotate relative to truck bed frame 34 and 36 via bearings, 33. An upper bar, 40 (FIG. 1) is attached to the truck 10. Between bar 40 and bar 30 is a hydraulic cylinder, 42, which places a load on assembly 20. As mentioned above, any suitable load supplying means can be used to pre-load auxiliary wheel 24 of assembly 20. Since truck 10 already operates with hydraulic lines, the use of hydraulic cylinder 42 is convenient and enables the truck operator to raise and lower assembly 20 remotely from within cab 16.

Figure 3:
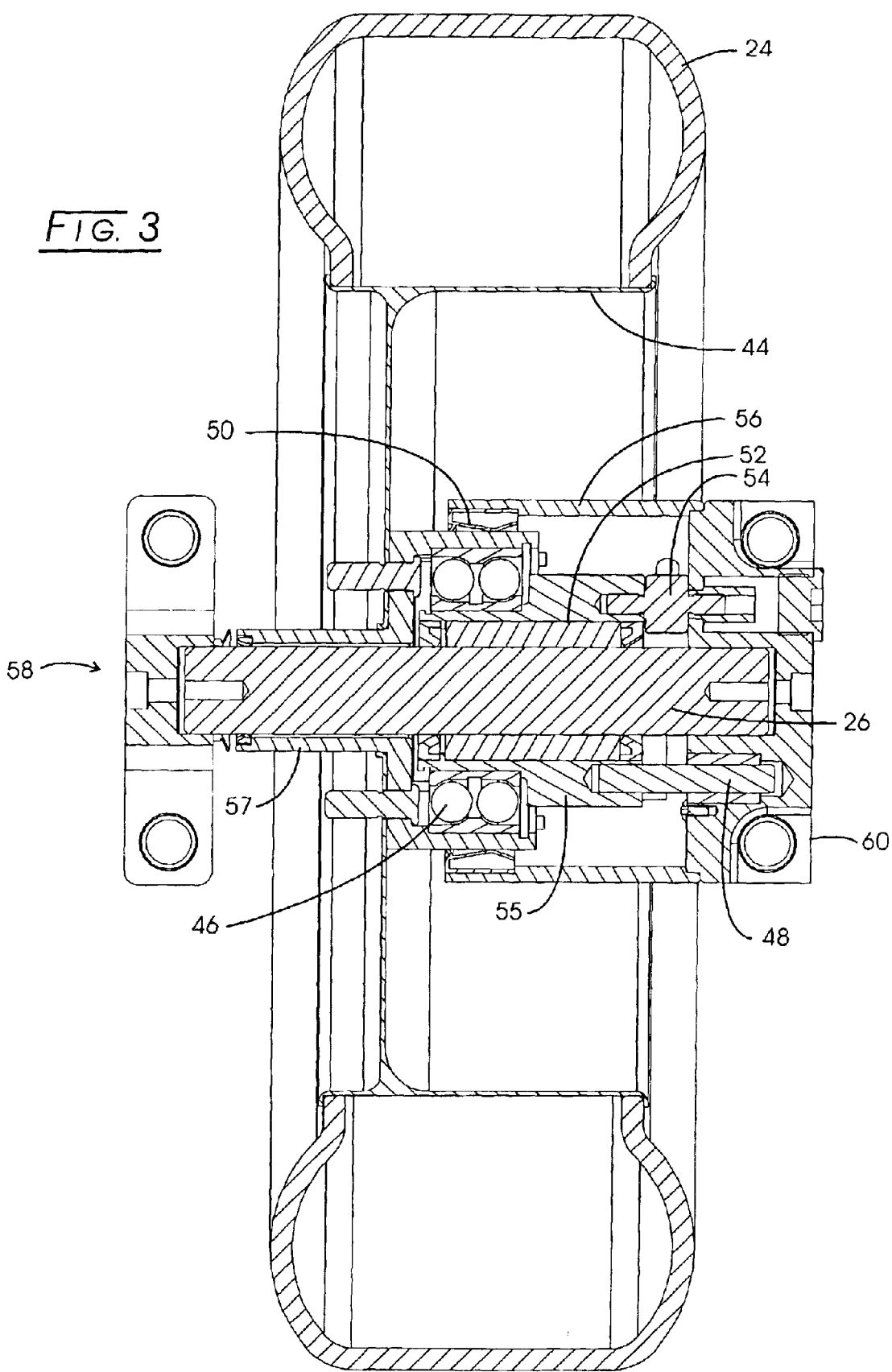
FIG. 3 is a cross-sectional view taken along line 3—3 of FIG. 2.

FIG. 3 displays one embodiment for isolating the axial forces placed on tire 24 and, thus, its corresponding wheel, 44, which is carried by a rotating hub, 57, and supported by axle 26. Assembly 20 is seen to include wheel bearings, 46, an anti-rotation linear bearing, 48, a non-rotating housing, 55, and a seal, 50. A linear bearing, 52, isolates housing 55 to moving axially under load. A load cell, 54, measures the axial force on tire 24 by the very small movement of housing 55 relative to the housing, 56, that retains all of the components just described. Finally, a pair of assemblies, 58 and 60, provide attachment to bars 28 and 30, respectively. Appropriate shimming, for example, of the respective mountings of 58 and 60 can set the toe-in of tire 24.

Figure 4:
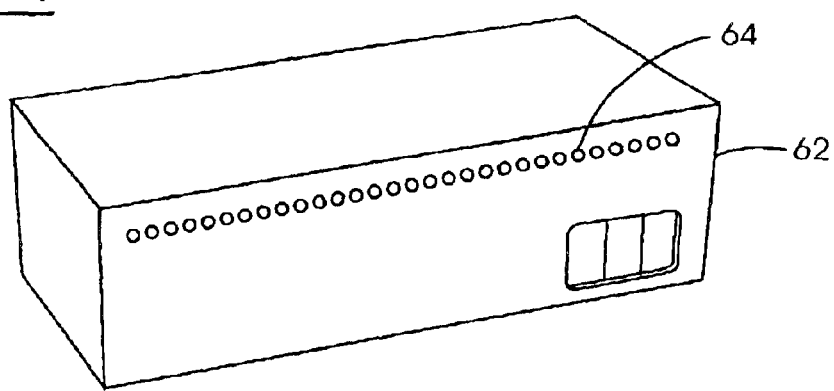
FIG. 4 is perspective elevational view of an output box mounted in the cab for viewing by the truck operator.

FIG. 4 depicts a converter/readout box, 62, that is mounted inside cab 16. A LED display, 64, provides the described 10 green, 10 yellow, and 10 red LED's that display road friction/slipperiness to the plow operator. An algorithm carried inside box 62 that correlates readout from load cell 54 to the road surface condition enables such display. Such algorithm is based on the data reported in the example and is empirical. A suitable microprocessor enables the algorithm to be utilized by the operator. Box 62 also has an input/output (I/O) port, e.g., RS232 port, for outputting its data, for example, to a telemetry system (e.g., transmitter and/or receiver) for transmitting the data back to a ground station, to a display for motorists, or the like. Readouts can include, for example, safety versus speed and road conditions.

Figure 5:
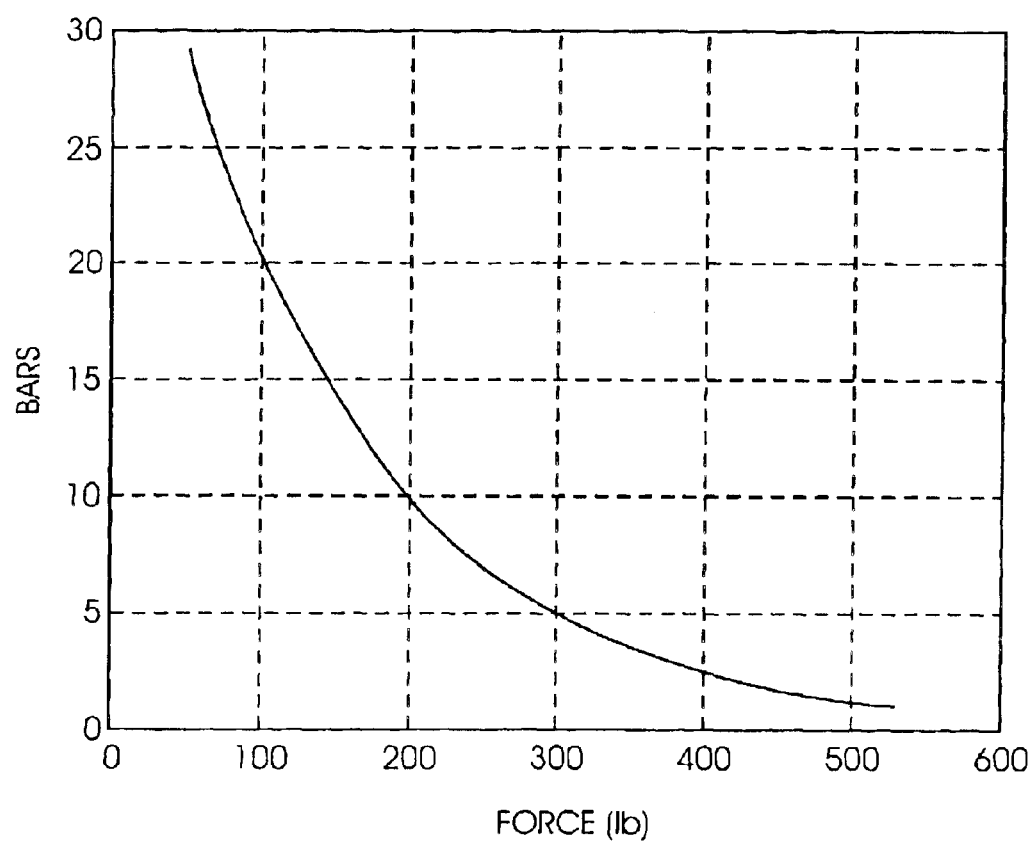
FIG. 5 graphically plots axial force exerted on the auxiliary wheel in pounds versus the number LED's or bars that are lit on the readout display to the vehicle operator.
Figure 6:
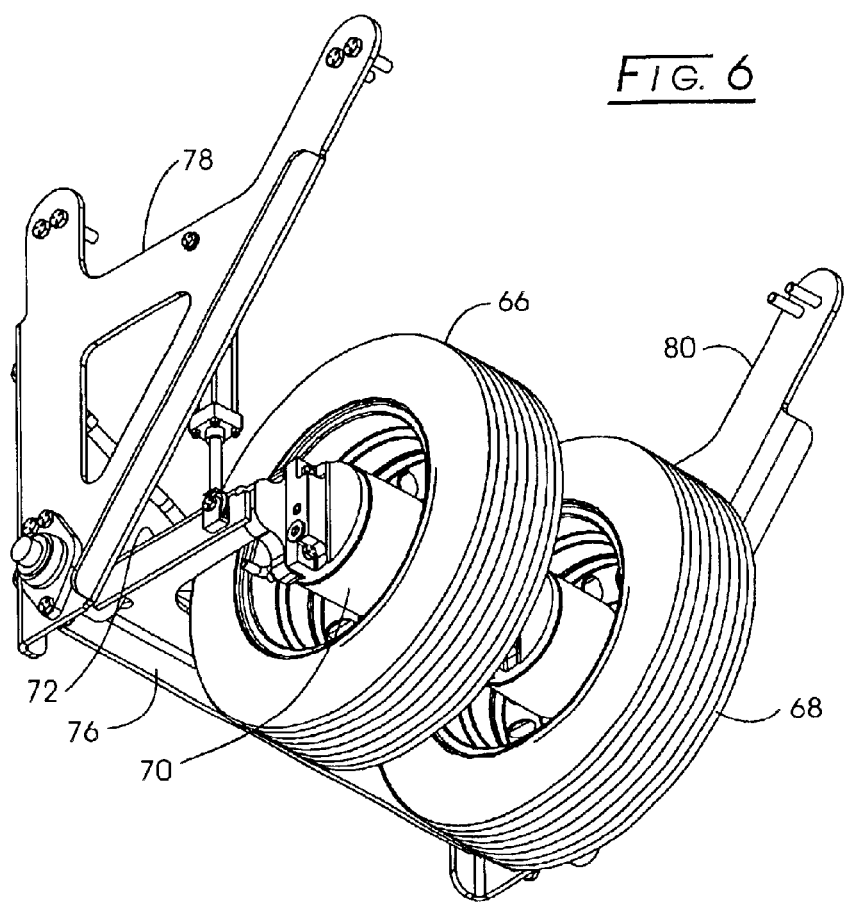
FIG. 6 is an alternative embodiment to FIGS. 2 and 3 showing an elevational view of a dual wheel RFT.
Figure 7:
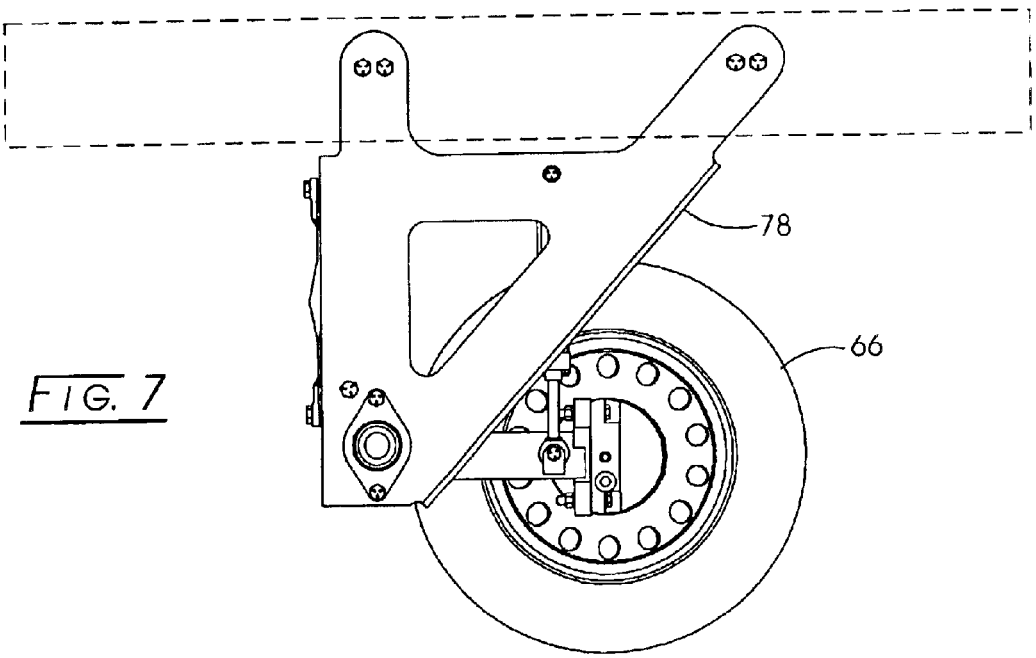
FIG. 7 is a side view of the dual wheel RFT of FIG. 6.

FIG. 5 graphically plots axial force exerted on the auxiliary wheel in pounds versus the number LED's or bars that are lit on the readout display to the vehicle operator based on data taken with the prototype unit reported in the Example on dry pavement. As the axial force decreases, the number of LED's lit increases, indicative of a loss of road friction. A key development was to correlate this graph with an actual road surface condition of ice, snow, or slush, for display to the truck operator. Such correlation is somewhat arbitrary in the definition of "ice", "slush, "snow", as it relates to safety of driving on such roadway surfaces. Nevertheless, empirical data taken with the prototype unit enabled an algorithm to be developed that successfully made this correlation. In this regard, the readout will enable the driver and/or a remote supervisor to order application of salt, sand, cinders, or other material to the roadway.

So far, the description of the invention has focused on truck 10 traveling in a straight line down a road. Real roads, however, have may turns, dips, bumps, and other twists that cause force to be exerted on the wheel unrelated to road surface condition. That is, the GEM device described above is designed to determine the grip force of a tire during the turn of a vehicle, such as a racecar. Truck 10 easily may be traveling on a curvy road that necessitates the RFT to properly determine the road surface condition even though the turn itself is adding auxiliary axial force to the device.

FIGS. 6–9 depict a dual wheel embodiment that could be used to determine road friction during turns of the vehicle. Specifically, a pair of wheels, 66 and 68, are seen carried to an axle, 70, whose ends are attached to the fingers, 72 and 74, of a U-shaped bracket, 76. A pair of triangular brackets, 78 and 80, respectively, mount to either end of bracket 76. Brackets 78 and 80 mount the assembly to the truck. A hydraulic cylinder, 82, mounts between bracket 78 and arm 72 to pre-load tires 66 and 68. A pair of crossbars, 84 and 86, span between the upper and lower ends of brackets 78 and 80 to complete a rugged structure.

Figure 8:
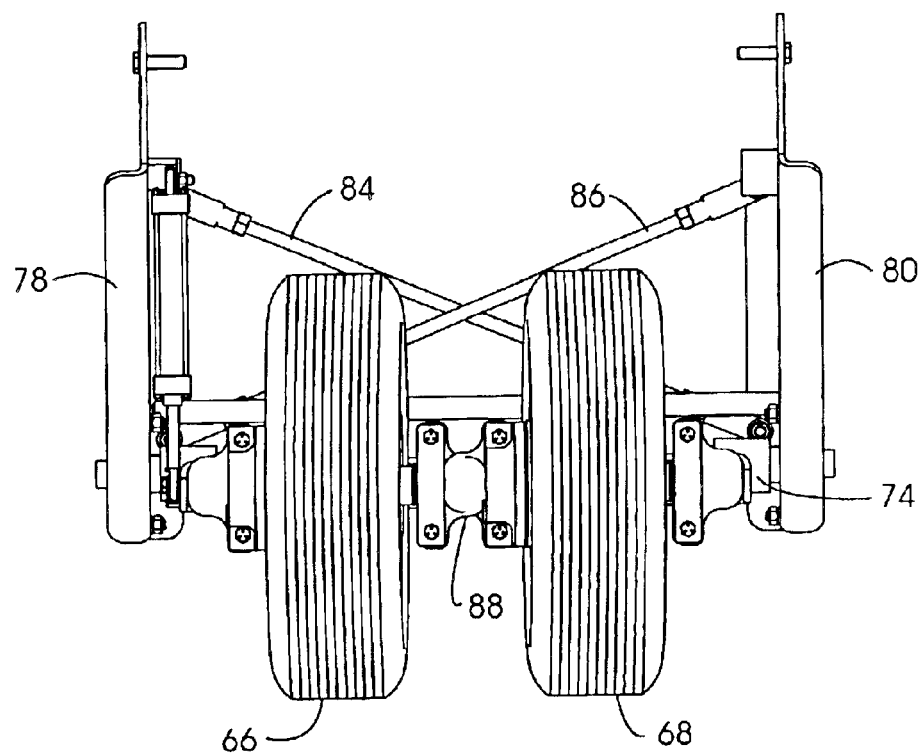
FIG. 8 is front elevational view of the dual wheel RFT of FIG. 6.
Figure 9:
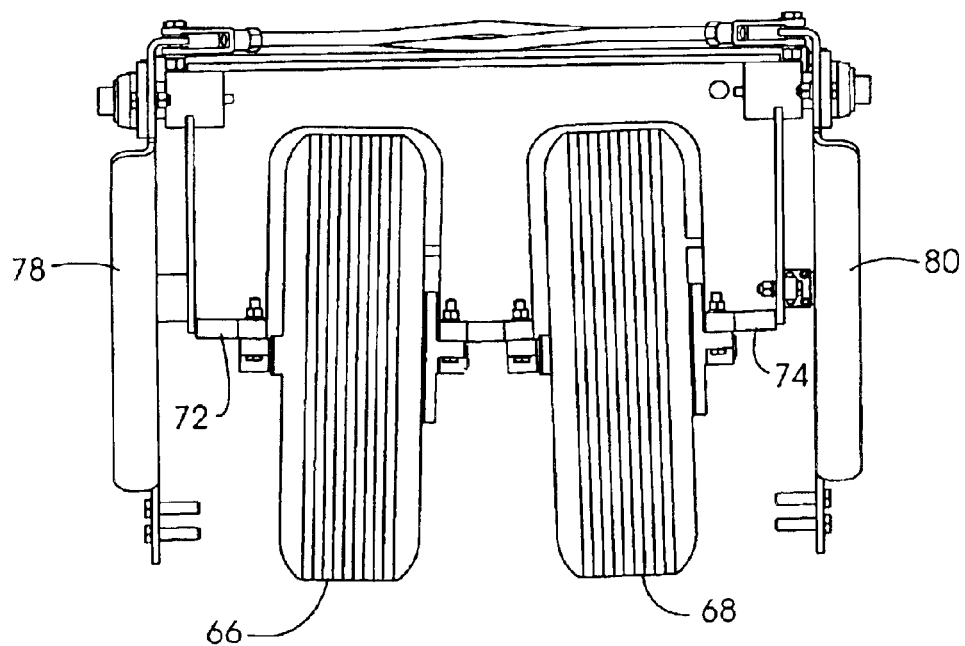
FIG. 9 is an overhead elevational view of the dual wheel RFT of FIG. 6.

As can be seen in FIGS. 8 and 9, a mounting assembly, 88, cooperates with mount and retains tires 66 and 68 in position. Proper toeing-in or towing out (e.g., between about 0.5° and 2.75°) of tires 66 and 68 also can be accomplished thereby. In design, tires 66 and 68 are toed in toward each other. This means that they will push towards each other during a straight-line traverse of the truck, but push in opposite directions during a turn. Such difference can be used to correlate road surface condition and subtract out the axial turning forces experienced by the truck during turns.

It will be appreciated that a wide variety of other axial load isolation schemes may be envisioned for use in the present RFT. While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the US system and all amounts and percentages are by weight, unless otherwise expressly indicated. Also, all citations referred herein are expressly incorporated herein by reference.

EXAMPLE

The tire used on the system is a standard production Bridgestone Insignia SL 185 65R14 tire mounted to a commercially available, standard automotive rim. The calibration and initial installation of the wheel was originally evaluated on dry pavement to assess relative load readings and vehicle handling interaction. The settings investigated were 450, 650, and 850 psi; toe settings of 1.25, 2.0, 2.75 degrees; and full tread, half tread, and minimum tread depth tires. From the data collected, it was apparent that higher vertical force on the tire resulted in less variation of the side force generated. Higher toe settings resulted in higher relative side loads. It also was apparent that toe angle settings of 2.75 degrees or greater was perceived by the driver as having an effect on vehicle handling. At this setting in dry conditions, the driver was able to detect the operation of the device as it caused the truck to alter its heading enough to require slight steering correction to maintain lane position. For this reason and others, such as tire wear, it was decided to limit the vertical force and toe setting of the tire to low values.

The physical properties of the tire are highly nonlinear. The side force generated is directly affected by vertical force and slip angle. The latter is a more nonlinear relationship. It is imperative for repeatable data that the tire toe and camber remain constant. The force measurement is taken almost directly from the thrust bearing inner race and is, therefore, quite dynamic and very sensitive. The orientation of the tire ensures that the thrust force is measured in only one direction while the vehicle is going straight down the road. When the vehicle is turned to the right (in the toe-in direction used), the value increases and it decreases toward zero and will traverse through zero when the vehicle is turned to the left. Static setup reveals that the system (tire not included) has very high sensitivity to thrust load and no measurable cross effect to vertical force on the tire.

Once the unit was proven on dry roads, the next step was to collect data on prepared low coefficient surfaces. This testing was performed at an automotive winter test facility. Facility personnel had prepared dry concrete, dry ice, and groomed snowfields for testing purposes. The particular day was sunny in the morning with increasing clouds; temperatures were in the teens and low twenties.

The test vehicle was a double axle International snowplow vehicle. It was equipped with solid de-icing hopper and spreader. It also was equipped with a Force America hydraulic system and ThomTech GPS system with data acquisition. The truck was washed thoroughly to minimize salt and grime contamination of the test grounds. To simulate loaded condition, the salt hopper was loaded with snow. Facility personnel prepared the grounds by removing fresh snow from the ice surfaces and paved areas and groomed the snowfields. Once the grounds were prepared, the truck operator was able to run over a prescribed course of dry concrete then directly onto a prepared ice pad. Driving on a groomed snowfield allowed the collection of snow friction data.

As both ice pads and the concrete pads were quite smooth, the pressure variation apparent in the pressure transducer trace was due to chassis motion. The snowfield was not nearly as smooth and the pressure variation and load generated were due to much more complex motion of the vehicle chassis and the terrain. To determine a value of friction for the different surfaces, the data was analyzed and lateral load points were chosen at the same time that the pressure trace crossed the pressure set point. A number of points were taken and averaged. This data was used to determine the basis of the cab display.

From many of the data traces, there appears to be an oscillation frequency of approximately 3.5 HZ in all data traces. This was assumed to be the natural frequency of the truck as loaded.

The snowfield data provided the most challenge in the determination of the actual friction value measured. The tire was set at 1.25 degrees toe and the pressure was set at 450 psi. The tire condition was new. The truck was run on roads with graded snow, slush, hard pack, and dry pavement. The automotive test facility results were confirmed when an accessible nearby locale had received fresh snow the evening before and the temperatures were near zero. All the roads had been plowed to a uniform depth of packed snow. Interestingly, the colder temperatures showed significantly higher friction values than warmer temperatures with similar conditions.

The measured data drove the development of a display for in cab mounting. It was in a graphic display. The final display developed for the prototype truck is a 30-segment bar graph with a 3-digit display of force in the right corner. The bar graph display consists of: 10 green LED's, 10 amber LED's, and 10 red LED's. The display operates as a data acquisition device. It collects force data at 100 Hz and performs an averaging process over 60 points. The result is displayed numerically and graphically. Currently, the bar graph relates information of friction such that the number of lit LED's increases as the force decreases and the relationship of number of LED's to force is a power function.

The data collected is summarized below:

TABLE 1

Data Assessment Load Value At The Pressure Set Point

|  | Pressure (psi) | Toe (°) | Tire | Surface | Load (lb) |
|---|---|---|---|---|---|
| Run No. | | | | | |
| 44 | 450 | 1.25 | New | Ice | 55 |
| 48 | 450 | 1.25 | New | Ice | 75 |
| 44 | 450 | 1.25 | New | Snow | 130 |
| 48 | 450 | 1.25 | New | Snow | 100 |
| 47 | 450 | 1.25 | New | Concrete | 235 |
| 14 | 450 | 1.25 | Half | Ice | 85 |
| 15 | 450 | 1.25 | Half | Snow | 130 |
| 14 | 450 | 1.25 | Half | Concrete | 400 |
| 27 | 450 | 1.25 | Worn Out | Ice | 85 |
| 28 | 450 | 1.25 | Worn Out | Ice | 95 |
| 28 | 450 | 1.25 | Worn Out | Snow | 130 |
| 27 | 450 | 1.25 | Worn Out | Snow | 150 |
| 26 | 450 | 1.25 | Worn Out | Concrete | 485 |
| Road | | | | | |
| Down 1 | 450 | 1.25 | New | Hard Pack | 200 |
| Down 2 | 450 | 1.25 | New | Hard Pack | 175 |
| Down 2 | 450 | 1.25 | New | Dry | 285 |
| Down 3 | 450 | 1.25 | New | Hard Pack | 155 |
| Down 3 | 450 | 1.25 | New | Slush | 200 |
| Down 4 | 450 | 1.25 | New | Hard Pack | 160 |

The system performed without any mechanical or electrical problems throughout the test. At no time did the unit adversely affect drivability or handling when the toe angle was set at 2 degrees or less. This was confirmed in 'blind' testing over extended periods. Not once did the driver notice or feel anything. Debriefing after testing also did not reveal any handling change with the unit deployed.

The unit was able to accurately resolve very low friction values. The variation in peak friction values on dry pavement with a new tire compared to a fully worn tire was quite marked. The new tire on dry pavement registered a force of 285 lb compared to 400 lb for a fully worn tire at 450 psi and 1.25 degrees. Because of this it is likely that all units will ship with tires with 50% of the tread removed.

I claim:

1. A method for measuring road surface friction of a road surface using a vehicle that moves across the road surface, which comprises the steps of:

(a) interposing an auxiliary independent wheel between said vehicle and the road surface, said auxiliary wheel being freely rotatable by movement of said vehicle and being one or more of toed in or toed out with respect to a direction of travel of said vehicle so as to create an isolated axial force on said auxiliary wheel;

(b) measuring the axial force on said auxiliary wheel while said vehicle moves across said road surface; and (c) correlating said measured axial force with the road surface friction.

2. The method of claim 1, wherein said interposing comprises:

(a1) mounting said auxiliary wheel on a single, non-rotating axle having a pair of ends, which axle ends are securely fastened to arms mounting said auxiliary wheel to said vehicle;

(a2) disposing a linear bearing around said axle to permit axial motion of said auxiliary wheel relative to said axle;

(a3) disposing said linear bearing in a non-rotating housing;

(a4) locating said auxiliary wheel in said housing so as to permit only axial movement of said auxiliary wheel;

(a5) providing a wheel bearing adjacent to said non-rotating housing;

(a6) supporting said auxiliary wheel with said housing, which sits outside of said wheel bearing; and (a7) disposing a force measuring cell between said non-rotating housing and said arms.

3. The method of claim 1, wherein the road surface is treated one or more of manually or automatically based on said measured axial force by.

4. The method of claim 3, wherein said road surface treatment involves application to the road surface of one or more of salt, brine, sand, or cinders.

5. The method of claim 1, wherein said measured axial force is transmitted to a remote location.

6. The method of claim 1, wherein said auxiliary wheel is one or more of toed in or toed out with respect to a direction of travel of said vehicle less than about 275°.

7. The method of claim 6, wherein said auxiliary wheel is one or more of toed in or toed out with respect to a direction of travel of said vehicle less than about 2°.

8. The method of claim 6, wherein said auxiliary wheel is one or more of toed in or toed out with respect to a direction of travel of said vehicle between about 0.5° and 275°.

9. The method of claim 1, wherein the speed of said vehicle is measured and, based on said speed and said measured axial force, a safe driving speed for said road surface is determined for one or more of said vehicle or for other vehicles by transmitting one or more of said speed and said measured axial force or said safe driving speed to a remote location.

10. The method of claim 1, wherein said interposing comprises:

(a1) spacing an upright and the axle apart;

(a2) disposing a load bearing assembly between said upright and said axle to allow axial mechanical freedom;

(a3) associating an axial thrust bearing assembly with said axle; and (a4) disposing a force sensor assembly between said axle thrust bearing assembly and said upright;

whereby the axial force on said auxiliary wheel is directly registered by said force sensor as said vehicle moves across the road surface.

11. A device for measuring road surface friction of a road surface using a vehicle that moves across the road surface, which comprises:

(a) an auxiliary independent wheel interposed between said vehicle and the road surface, said auxiliary wheel being freely rotatable by movement of said vehicle and being one or more of toed in or toed out with respect to a direction of travel of said vehicle so as to create an axial force on said auxiliary wheel;

(b) an axial force sensor mounted with respect to said auxiliary wheel so as to measure the axial force exerted on said auxiliary wheel while said vehicle moves across said road surface; and (c) a converter for correlating the measured axial force with the road surface friction.

12. The device of claim 11, wherein:

(a1) said auxiliary wheel is mounted on a single, non-rotating axle having a pair of ends, which axle ends are securely fastened to arms mounting said auxiliary wheel to said vehicle;

(a2) a linear bearing is disposed around said axle to permit axial motion of said auxiliary wheel relative to said axle;

(a3) said linear bearing is disposed in a non-rotating housing;

(a4) said auxiliary wheel is located in said housing so as to permit only axial movement of said auxiliary wheel;

(a5) a wheel bearing is provided adjacent to said housing;

(a6) said auxiliary wheel is supported with said housing, which sits outside of said wheel bearing; and (b1) a force measuring cell is disposed between said housing and said arms.

13. The device of claim 11, wherein said device is associated a transmitter for transmitting said measured axial force to a remote location.

14. The device of claim 13, wherein said auxiliary wheel is one or more of toed in or toed out with respect to a direction of travel of said vehicle less than about 2.75°.

15. The device of claim 14, wherein said auxiliary wheel is one or more of toed in or toed out with respect to a direction of travel of said vehicle less than about 2°.

16. The device of claim 11, wherein said auxiliary wheel is one or more of toed in or toed out with respect to a direction of travel of said vehicle between about 0.5° and 2.75°.

17. A method for measuring road surface friction, which comprises the steps of:

(a) providing a vehicle;

(b) mounting an auxiliary wheel to said vehicle, said auxiliary wheel being one or more of toed in or toed out, loaded, and mounted on an axle for its free rolling;

(c) associating a speed device and a calibrated force sensor with said auxiliary wheel to measure the axial force thereon;

(d) moving said vehicle along a road; and (e) determining the road surface friction based on the speed of said auxiliary wheel and the lateral force exerted on said auxiliary wheel.

18. The method of claim 17, wherein said vehicle is equipped to spread one or more of salt, brine, sand, or cinders, onto the road surface.

19. The method of claim 17, which further includes the steps of:

(a1) mounting said auxiliary wheel on a single, non-rotating axle having a pair of ends, which axle ends are securely fastened to arms mounting said auxiliary wheel to said vehicle;

(a2) disposing a linear bearing around said axle to permit axial motion of said auxiliary wheel relative to said axle;

(a3) disposing said linear bearing in a non-rotating housing;

(a4) locating said auxiliary wheel in said housing so as to permit only axial movement of said auxiliary wheel;

(a5) providing a wheel bearing adjacent to said housing;

(a6) supporting said auxiliary wheel with said housing, which sits outside of said wheel bearing; and (a7) disposing a force measuring cell between said housing and said arms.

20. The method of claim 17, wherein the road surface is treated based on said determined road surface friction.

21. The method of claim 17, wherein said road surface treatment involves application to the road surface of one or more of salt, brine, sand, or cinders.

22. The method of claim 17, wherein said determined road surface friction is transmitted to a remote location.

23. The method of claim 17, wherein said auxiliary wheel is one or more of toed in or toed out with respect to a direction of travel of said vehicle less than about 2.75°.

24. The method of claim 23, wherein said auxiliary wheel is one or more of toed in or toed out with respect to a direction of travel of said vehicle less than about 2°.

25. The method of claim 24, wherein said auxiliary wheel is one or more of toed in or toed out with respect to a direction of travel of said vehicle between about 0.5° and 2.75°.

26. In combination, a vehicle and a device affixed to said vehicle, said device for measuring road surface friction, said device comprising:

(a) an auxiliary wheel mounted to said vehicle, said auxiliary wheel being one or more of toed in or toed out, loaded, and mounted on an axle for its free rolling;

(b) a calibrated force sensor associated with said auxiliary wheel to measure the axial force thereon;

(c) a converter for measuring the road surface friction with said force sensor.

27. The combination of claim 26, which further comprises:

(a1) said auxiliary wheel is mounted on a single, non-rotating axle having a pair of ends, which axle ends are securely fastened to arms mounting said auxiliary wheel to said vehicle;

(a2) a linear bearing is disposed around said axle to permit axial motion of said auxiliary wheel relative to said axle;

(a3) said linear bearing is disposed in a non-rotating housing;

(a4) said auxiliary wheel is located in said housing so as to permit only axial movement of said auxiliary wheel;

(a5) a wheel bearing is provided adjacent to said housing;

(a6) said auxiliary wheel is supported with said housing, which sits outside of said wheel bearing; and (b1) said force sensor is disposed between said housing and said arms.

28. The combination of claim 26, wherein the road surface is treated based on said measured axial force.

29. The combination of claim 28, wherein said road surface treatment involves application to the road surface of one or more of salt, brine, sand, or cinders.

30. The combination of claim 26, wherein said measured axial force is transmitted to a remote location.

31. The combination of claim 26, wherein said auxiliary wheel is one or more of toed in or toed out with respect to a direction of travel of said vehicle less than about 2.75°.

32. The combination of claim 27, wherein said auxiliary wheel is one or more of toed in or toed out with respect to a direction of travel of said vehicle less than about 2°.

33. The combination of claim 28, wherein said auxiliary wheel is one or more of toed in or toed out with respect to a direction of travel of said vehicle between about 0.5° and 2.75°.

\* \* \* \* \*